United States Patent
Bardy et al.

(10) Patent No.: US 7,085,601 B1
(45) Date of Patent: Aug. 1, 2006

(54) EXTERNAL ATRIAL DEFIBRILLATOR AND METHOD FOR PERSONAL TERMINATION OF ATRIAL FIBRILLATION

(75) Inventors: Gust H. Bardy, Seattle, WA (US); George Klein, London (CA)

(73) Assignee: Koninklijke Philips Electronics N.V., Eindhoven (NL)

( * ) Notice: Subject to any disclaimer, the term of this patent is extended or adjusted under 35 U.S.C. 154(b) by 587 days.

(21) Appl. No.: 09/441,936

(22) Filed: Nov. 17, 1999

(51) Int. Cl.
*A61N 1/39* (2006.01)

(52) U.S. Cl. ............................................. 607/5
(58) Field of Classification Search ........ 600/508–509, 600/516–520; 607/4–5, 7, 63, 115, 142
See application file for complete search history.

(56) References Cited

U.S. PATENT DOCUMENTS

| | | | | | |
|---|---|---|---|---|---|
| 3,442,269 | A | * | 5/1969 | Druz | 607/2 |
| 3,453,745 | A | * | 7/1969 | Spivak | 434/262 |
| 3,633,569 | A | * | 1/1972 | Brayshaw et al. | 600/515 |
| 4,202,340 | A | * | 5/1980 | Langer et al. | 607/5 |
| 4,610,254 | A | * | 9/1986 | Morgan et al. | 607/6 |
| 4,984,572 | A | * | 1/1991 | Cohen | 607/6 |
| 5,207,219 | A | * | 5/1993 | Adams et al. | 607/5 |
| 5,269,301 | A | * | 12/1993 | Cohen | 607/6 |
| 5,370,667 | A | | 12/1994 | Alt | 607/19 |
| 5,403,353 | A | * | 4/1995 | Alferness et al. | 607/5 |
| 5,490,862 | A | * | 2/1996 | Adams et al. | 607/6 |
| 5,509,925 | A | * | 4/1996 | Adams et al. | 600/518 |
| 5,735,879 | A | | 4/1998 | Gliner et al. | 607/7 |
| 5,792,205 | A | * | 8/1998 | Alt et al. | 607/32 |
| 5,817,132 | A | * | 10/1998 | Karagueuzian et al. | 607/5 |
| 5,824,033 | A | * | 10/1998 | Ferrari | 607/142 |
| 5,928,270 | A | * | 7/1999 | Ramsey, III | 607/5 |
| 6,068,651 | A | * | 5/2000 | Brandell | 607/5 |
| 6,141,581 | A | * | 10/2000 | Olson et al. | 600/515 |
| 6,181,967 | B1 | * | 1/2001 | Alt | 607/5 |
| 6,292,692 | B1 | * | 9/2001 | Skelton et al. | 607/2 |

* cited by examiner

*Primary Examiner*—Kennedy Schaetzle
*Assistant Examiner*—Kristen Mullen
(74) *Attorney, Agent, or Firm*—Tony Piotrowski

(57) ABSTRACT

An atrial defibrillator includes a portable, non-implantable housing, a pair of defibrillator pads, a shock generator, and an analyzer. The pads are applied to the outside of a patient's body, and the shock generator delivers a shock to the patient via the pads. The analyzer receives a cardiac signal from the patient, determines from the signal whether the patient is experiencing atrial fibrillation, and enables the shock generator if the patient is experiencing atrial fibrillation. Unlike conventional external atrial defibrillators, such an atrial defibrillator can be used by a layperson in the comfort of a patient's own home. Furthermore, such a defibrillator does not cause the surgery-related problems associated with implantable atrial defibrillators. Moreover, because the patient can choose when to receive a shock, such a defibrillator is less likely to surprise and embarrass the patient than automatic implantable defibrillators are.

18 Claims, 7 Drawing Sheets

EXTERNAL ATRIAL DEFIBRILLATOR AND METHOD FOR PERSONAL TERMINATION OF ATRIAL FIBRILLATION

TECHNICAL FIELD

The invention relates generally to medical devices, and more particularly to an external atrial defibrillator and method for terminating atrial fibrillation.

BACKGROUND OF THE INVENTION

Atrial fibrillation (AF), which lay persons know as heart palpitations, is a commonly occurring cardiac arrhythmia. Generally, an AF episode is not life threatening, and the patient is functional during the episode. Some patients, however, feel under the weather, feel dizzy, or even lose consciousness during an AF episode. Nevertheless, even in the most severe cases, AF episodes without secondary sequelae and lasting less than 48 hours are thought to have no long-term adverse effects on a patient's health. Conversely, among other consequences, episodes lasting 48 hours or longer increase a patient's risk of stroke. Therefore, a patient's physician usually instructs him/her to seek medical treatment if an AF episode does not spontaneously terminate within 24 hours. This gives the patient sufficient time to actually receive treatment within the 48-hour safety window.

Referring to FIGS. 1 and 2, AF is characterized by irregularly distributed R—R intervals in a patient's electrocardiogram. FIG. 1 is portion of a patient's electrocardiogram that includes one R—R interval. The electrocardiogram includes P, Q, R, S, and T waves, and the R—R interval is defined as the interval between the upper peaks of adjacent R waves. FIG. 2 is a plot of the respective lengths of a patient's R—R intervals during an AF episode. In the electrocardiogram of a patient having a normal heart rhythm, the lengths of adjacent R—R intervals differ from one another by no more than a few milliseconds (ms), and thus are approximately equal. Therefore, during a period of normal heart rhythm, the plotted lengths of the R—R intervals would lie on or near the dashed line 10 in a normal distribution pattern. But during an AF episode, the plotted lengths of the R—R intervals differ significantly and randomly from one another. Therefore, during an AF episode, the plotted lengths 12 of the R—R intervals lie in a random distribution pattern with the appearance of a "bee swarm".

There are several preventative and termination treatments available to patients with AF. Preventative treatments such as anti-arrhythmic drug therapy help prevent AF episodes from occurring, and termination treatments such as cardioversion terminate AF episodes once they have begun. As discussed below, some of these treatments are often expensive and/or inconvenient.

An external atrial defibrillator is a device that a cardiologist uses to apply one or more cardioverting electrical pulses, i.e., shocks, to the patient in order to terminate an AF episode. As discussed above, the cardiologist instructs his patient to notify the cardiologist's office if an AF episode lasts more than 24 hours. The cardiologist then admits the patient to the hospital on an in-patient or out-patient basis. While in the hospital, the patient is anesthetized and is shocked one or more times until the AF episode terminates. Unfortunately, this procedure costs approximately $1000–$5000 per session depending upon the procedure location within the hospital, and thus is relatively expensive. In addition, this procedure is burdensome to the patient for a number of reasons. For example, he/she often misses at least a day of work to undergo cardioversion. Furthermore, because the lingering effects of the anesthesia render him/her temporarily unfit to drive, the patient must find someone to drive him/her home from the hospital after the procedure. Because many AF patients require this procedure several times per year, the cumulative costs and burdens associated with this procedure can be quite substantial.

An internal atrial defibrillator is a device that is implanted within a patient's body and that applies one or more cardioverting electrical shocks directly to the patient's heart in order to terminate an AF episode. A manual model, such as the InControl Metrix, allows the patient to shock himself when he wishes to terminate an AF episode. In one known device, the patient initiates a shock by using a magnet to toggle a subcutaneous switch. Unfortunately, the implant surgery may cause discomfort to the patient, and complications such as infection may arise following surgery. Furthermore, additional surgeries can be required to replace the batteries or to repair or replace a defective unit. Alternatively, the internal defibrillator may include circuitry that detects an AF episode and automatically shocks the patient to terminate it. Unfortunately, in addition to the problems described above for the manual model, the automatic model may embarrass the patient. For example, a defibrillator shock affects not only the heart muscle, but often contracts most, if not all, of the voluntary muscles in the patient's thorax. Unfortunately, these contractions often cause the patient to "jump" uncontrollably. Therefore because the patient has no control over when the defibrillator delivers the shock, the shock, and thus this potentially embarrassing side effect, may occur during work or a social occasion.

Therefore, what is needed is an external atrial defibrillator that a patient or caretaker can use safely in the patient's own home.

SUMMARY OF THE INVENTION

In one aspect of the invention, an atrial defibrillator includes a pair of defibrillator pads, a shock generator, and an analyzer. The pads are applied to the outside of a patient's body, and the shock generator delivers a shock to the patient via the pads. The analyzer receives a cardiac signal from the patient, determines from the signal whether the patient is experiencing atrial fibrillation, and enables the shock generator if the patient is experiencing atrial fibrillation.

Unlike conventional external atrial defibrillators, such an atrial defibrillator can be used by a layperson in the comfort of a patient's own home. Furthermore, such a defibrillator does not cause the surgery-related problems associated with implantable atrial defibrillators. Moreover, because the patient can choose when to receive a shock, such a defibrillator is less likely to embarrass the patient than automatic implantable defibrillators are.

DESCRIPTION OF THE INVENTION

Figure 3:
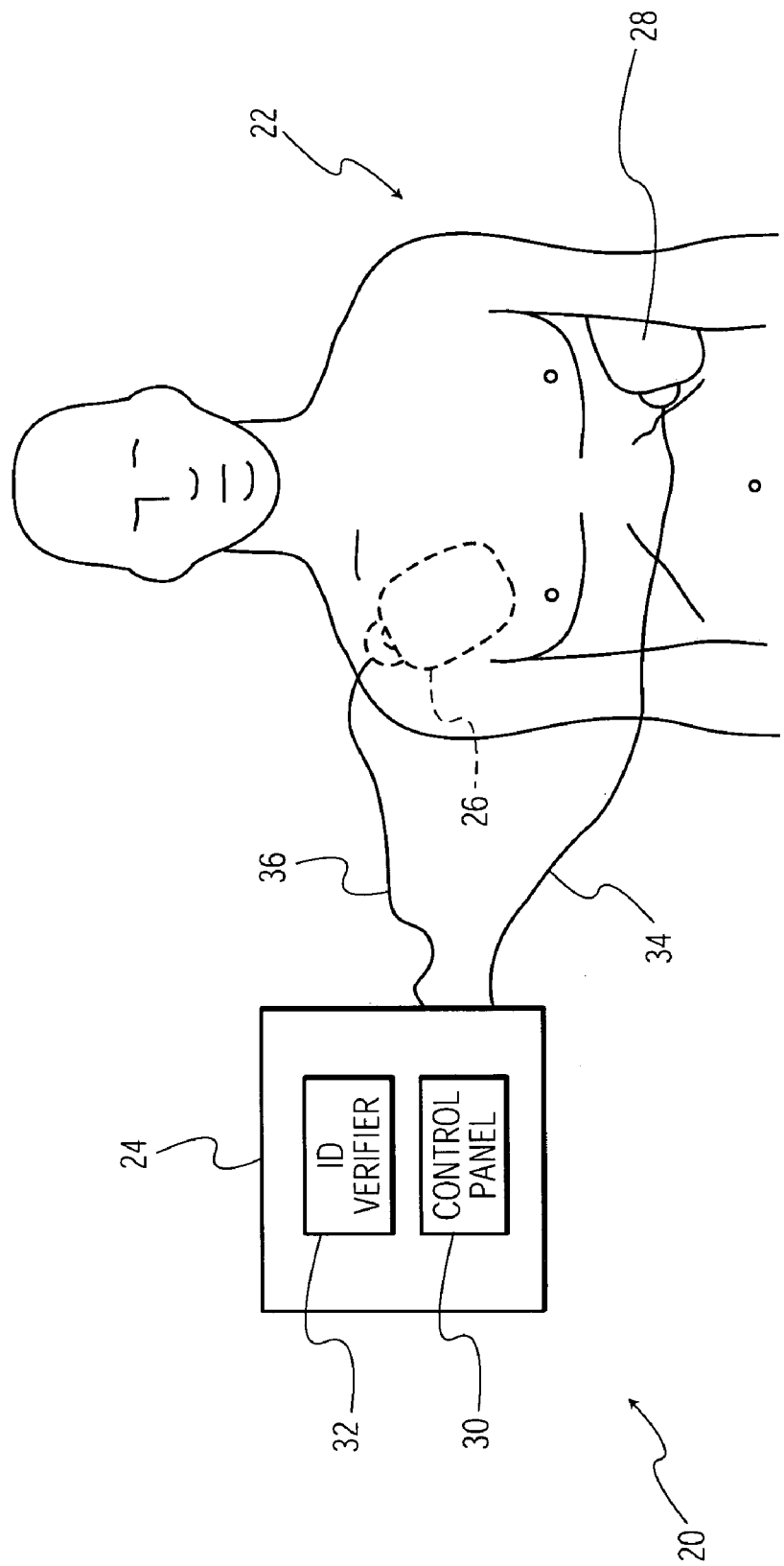
FIG. 3 is a diagram of an atrial defibrillator according to an embodiment of the invention, and a patient connected to the defibrillator.

FIG. 3 is a block diagram of an atrial defibrillator 20 according to an embodiment of the invention, and a patient 22 connected thereto. The defibrillator 20 includes a portable shock/analyze unit 24 for generating an atrial-defibrillation (ADF) shock, and includes electrode pads 26 and 28 for delivering the ADF shock to the patient 22. (The pad 26 is in dashed line to indicate that it is coupled to the patent's back.) The unit 24 includes a control panel 30, which allows an operator (not shown) to input commands such as a shock command to the unit 24, and includes an identification verifier 32, which prevents the unit 24 from generating a shock if the operator is unauthorized to operate the unit. The pads 26 and 28 are coupled to the unit 24 via wires 34 and 36, respectively, are attached to the patient 22 with a conventional adhesive, and include a conventional contact gel that enhances the electrical conductivity between the pads and the patient's skin. Although an anterior-posterior placement of the pads 26 and 28 is shown and is believed to be the most effective placement for terminating an AF episode, one can use the shock unit 24 with other pad placements as well.

In operation, the shock/analyze unit 24 analyzes the patient's heart rhythm, determines whether the patient 22 is experiencing an AF episode, and generates an ADF shock in response to the operator's command if the patient 22 is experiencing an AF episode and other conditions are met. The unit 24 receives a cardiac signal such as an electrocardiogram from the patient 22 via the pads 26 and 28 or by other conventional means. The unit 24 analyzes the cardiac signal to determine whether the patient is experiencing an AF episode. If the patient is experiencing an AF episode, then the identification verifier 32 determines whether the operator is authorized to shock the patient 22. If the operator is authorized, the unit 24 generates an ADF shock in response to the operator entering a shock command via the panel 30. As discussed below in conjunction with FIGS. 4 and 5, the verifier 32 checks the operator's authorization primarily for safety reasons. For example, in one embodiment the verifier 32 prevents the patient 22 from shocking himself/herself. After generating the ADF shock, the unit 24 analyzes the cardiac signal again to determine whether the AF episode has terminated, informs the operator and patient of the analysis results, and suggests further treatment options if the AF episode has not terminated. Conversely, if the patient 22 is not experiencing an AF episode or if the operator is unauthorized to operate the defibrillator 20, then the unit 24 does not generate an ADF shock regardless of the commands that the operator enters via the panel 30.

The atrial defibrillator 20 provides many advantages over prior atrial defibrillators. Unlike conventional external defibrillators, the portability and analysis capability of the shock/analyze unit 24 make the defibrillator 20 ideal for use by laypersons outside of the hospital and doctor's office. Therefore, the defibrillator 20 significantly reduces the costs and inconveniences associated with conventional external cardioversion techniques, and may even be a convenient alternative to anti-arrhythmic drug therapy for some patients. Furthermore, unlike implantable atrial defibrillators, the defibrillator 20 has no surgery-related risks and allows the patient 22 to receive an ADF shock at a time and place of his/her own choosing.

Although one embodiment of the defibrillator 20 is discussed for example purposes, the inventors contemplate other embodiments. For example, the unit 24 may lack the non-patient operator verifier 32 so that the patient 22 can shock himself/herself should the diagnostic algorithm allow.

Figure 4:
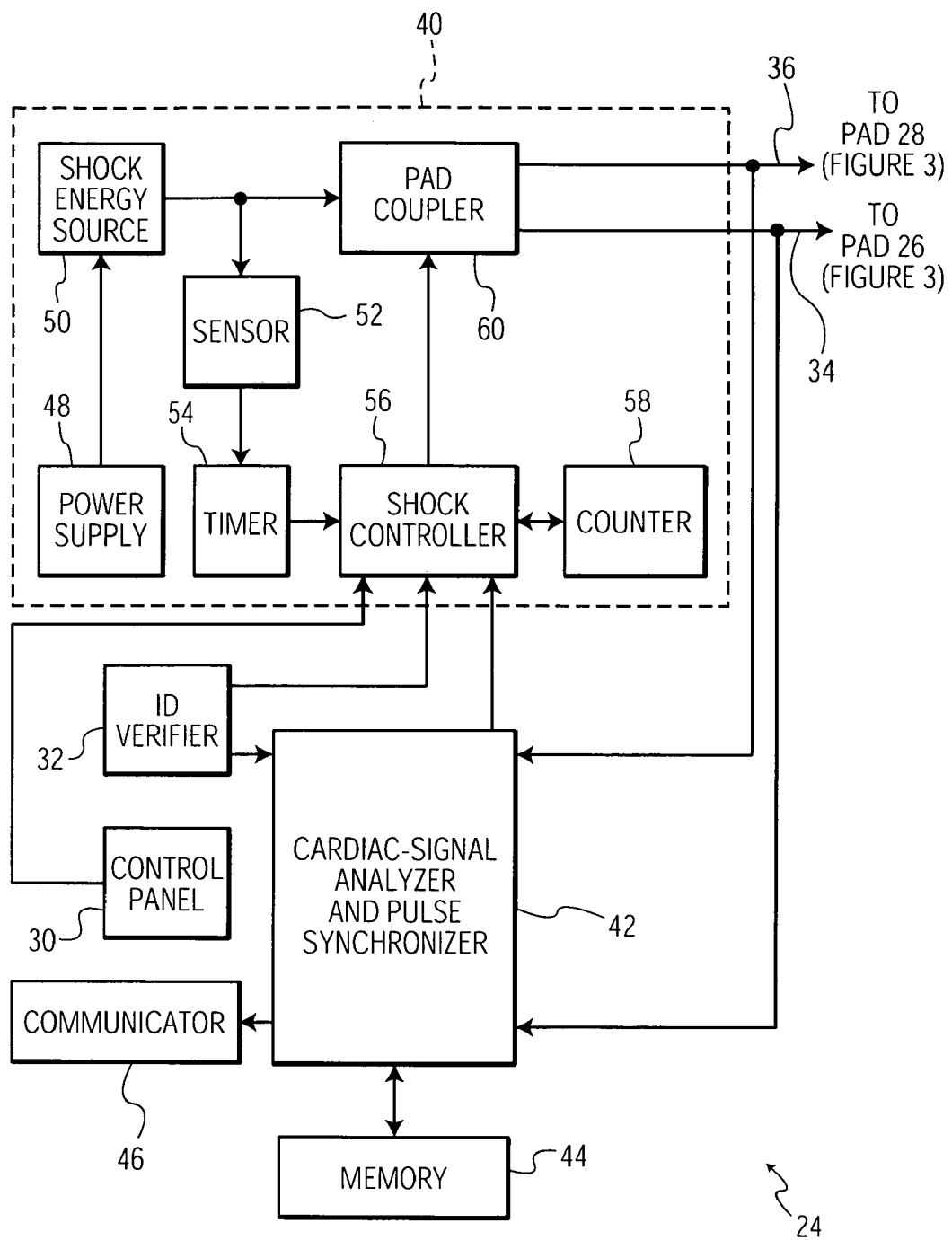
FIG. 4 is a schematic block diagram of the atrial defibrillator of FIG. 3 according to an embodiment of the invention.

FIG. 4 is a schematic block diagram of the shock/analyze unit 24 of FIG. 3 according to an embodiment of the invention. In addition to the control panel 30 and the identification verifier 32, the unit 24 includes a shock-generator circuit 40, an analyze/synchronize circuit 42, a memory 44, and a communicator 46.

In operation, the circuit 42 first analyzes the cardiac signal from the patient 22 via the pads 26 and 28 (FIG. 3) to determine if the patient is experiencing an AF episode. If the patient 22 is not experiencing an AF episode, then the circuit 42 informs the patient and operator via the communicator 46—which may be a visual display or a speech synthesizer—and the unit 24 delivers no ADF shocks. If the patient is experiencing an AF episode, the circuit 42 informs the patient and operator via the communicator 46, enables the circuit 40, and synchronizes the circuit 40 such that it generates the ADF shock during a desired portion of the cardiac signal. Thus, even if the operator enters a shock command via the control panel 30, the circuit 42 delays the circuit 40 from generating the ADF shock until the occurrence of the desired portion of the cardiac signal. After the ADF shock, the circuit 42 analyzes the cardiac signal to determine if the AF episode has terminated. If it has, the circuit 42 informs the patient and operator via the communicator 46 and disables the circuit 40 from generating more ADF pulses. If the AF episode has not terminated, the circuit 42 informs the patient and operator and allows the circuit 40 to generate another ADF shock if the patient so desires. But as discussed below, the circuit 42 may disable the circuit 40 after the patient has received a predetermined maximum number of ADF shocks.

Still referring to FIG. 4, the design and operation of the shock-generator circuit 40 and the analyze/synchronize circuit 42 are discussed in more detail.

In one embodiment, the shock-generator circuit 40 is conventional and includes a power supply 48, shock source 50, sensor 52, timer 54, controller 56, counter 58, and pad coupler 60. The supply 48 charges the shock source 50, and in the absence of another power supply, provides power to the other circuitry of the shock/analyze unit 24. When the pad coupler 60 couples the source 50 to the wires 34 and 36, the shock source 50, which is a capacitor bank in one embodiment, discharges to generate an ADF shock pulse. The sensor 52 provides a sensor signal to the timer 54 when the pulse decays to a predetermined level. The timer 54 provides a pulse timing signal to the controller 54. The controller 56 activates the pad coupler 60 to generate an ADF pulse, deactivates the pad coupler 58 to terminate an ADF pulse, and may reverse the polarity of the coupler 58 to reverse the polarity of a biphasic or multiphasic ADF pulse. The counter 58 increments or decrements by one each time the controller 56 activates the pad coupler 58 to generate a new ADF pulse.

In operation, when it receives respective enable signals from the identification verifier 32, the analyzer 44, and the counter 58, the shock controller 56 activates the pad coupler 60 in response to a shock command from the control panel 30. The active coupler 60 couples the shock source 50 to the pads 26 and 28, and thus the energy stored in the source 50 discharges into the patient 22 (FIG. 3). This transfer of energy constitutes the ADF pulse. The sensor 52 monitors the ADF pulse, and, when it decays to a predetermined level, the sensor 52 signals the timer 54. The timer 54 waits a predetermined time after receiving the sensor signal, and then provides a timing signal to the controller 56. If the controller 56 is programmed to generate a uniphasic ADF pulse, then the controller 56 deactivates the pulse coupler 60, which uncouples the shock source 50 from the pads 26 and 28 to terminate the pulse. If, on the other hand, the controller 56 is programmed to generate a biphasic ADF pulse, then the controller 56 causes the pulse coupler 60 to reverse the polarity of the connection between the shock source 50 and the pads 26 and 28. The sensor 52 then monitors this reversed-polarity portion of the pulse, and, when this portion of the pulse decays to a predetermined level, the sensor 52 again signals the timer 54. The timer 54 waits a predetermined time after receiving the sensor signal and then provides another timing signal to the controller 56, which deactivates the pulse coupler 60 to terminate the biphasic ADF pulse. Although the shock controller 56 is described as generating uniphasic or biphasic ADF pulses, the shock controller 56 can also generate multiphasic ADF pulses in a similar manner.

As is known, the ADF pulses generated by the shock-generator circuit 40 can have a wide range of voltage and energy levels. For example, the energy levels of ADF pulses are typically within a range of approximately 70–400 Joules (J). Because AF episodes are difficult to terminate with one ADF pulse, particularly with a lower-energy pulse, in one embodiment the circuit 40 generates each ADF pulse having an energy of at least 200 J. This reduces the chance that the patient will require multiple ADF pulses to terminate an AF episode. Typically, multiple pulses are more uncomfortable to a patient than a single pulse, even if the single pulse has a higher energy level than each of the multiple pulses. Therefore, terminating an AF episode in only one pulse significantly reduces the patient's discomfort.

Shock-generator circuits such as the shock-generator circuit 40 are discussed in many references including U.S. Pat. No. 5,735,879 to Gliner et al. for "Electrotherapy Method for External Defibrillators", which is incorporated by reference.

Still referring to FIG. 4, as discussed above, the analyze/synchronize circuit 42 analyzes a cardiac signal to determine if the patient 22 is experiencing an AF episode, and if so, enables the shock-generator circuit 40 and synchronizes the generation of the ADF pulse to the cardiac signal. If, on the other hand, the patient is not experiencing an AF episode or has received the maximum number of ADF pulses allowed, the circuit 42 may disable the circuit 40 from generating another ADF shock.

Figure 1:
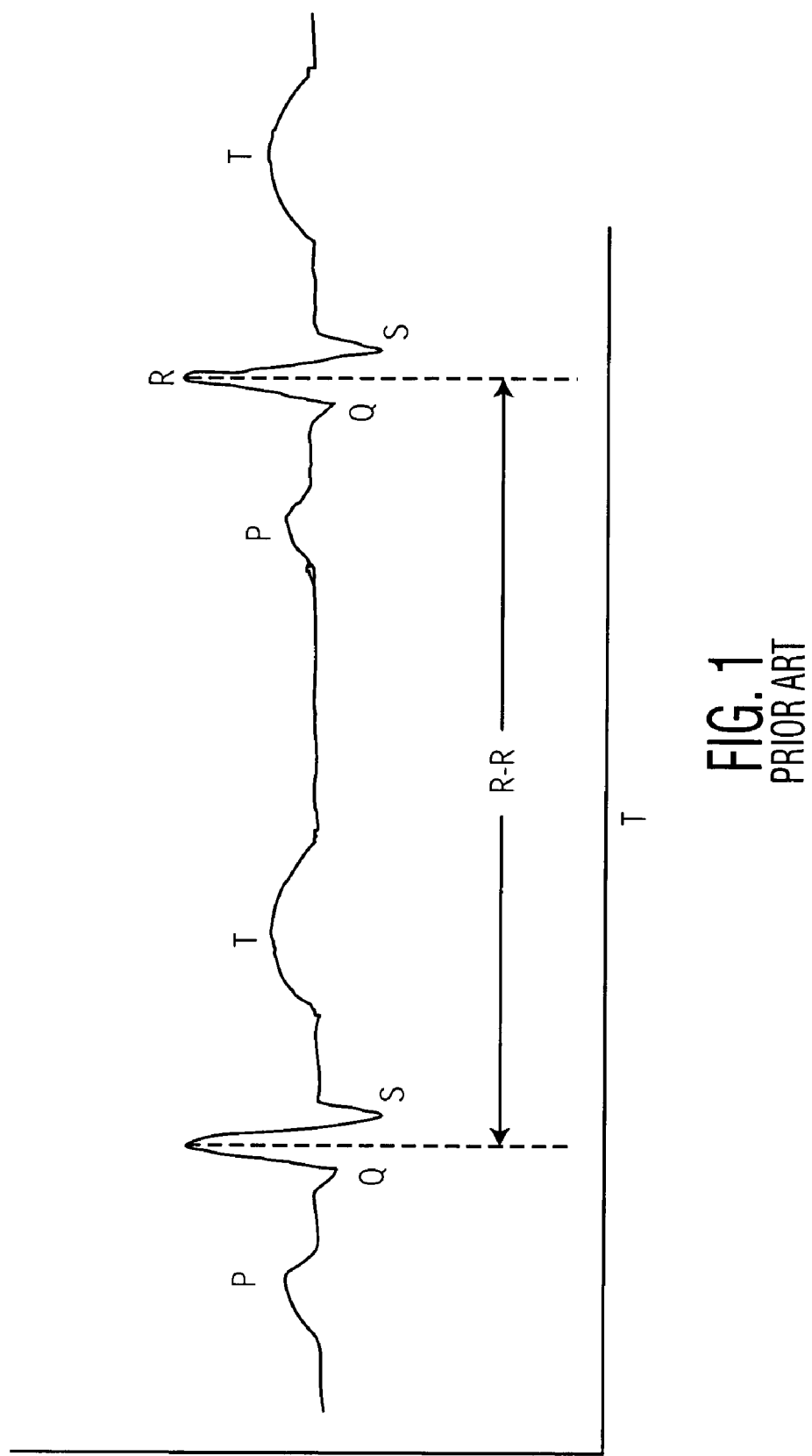
FIG. 1 is portion of a patient's electrocardiogram that includes an R—R interval.
Figure 2:
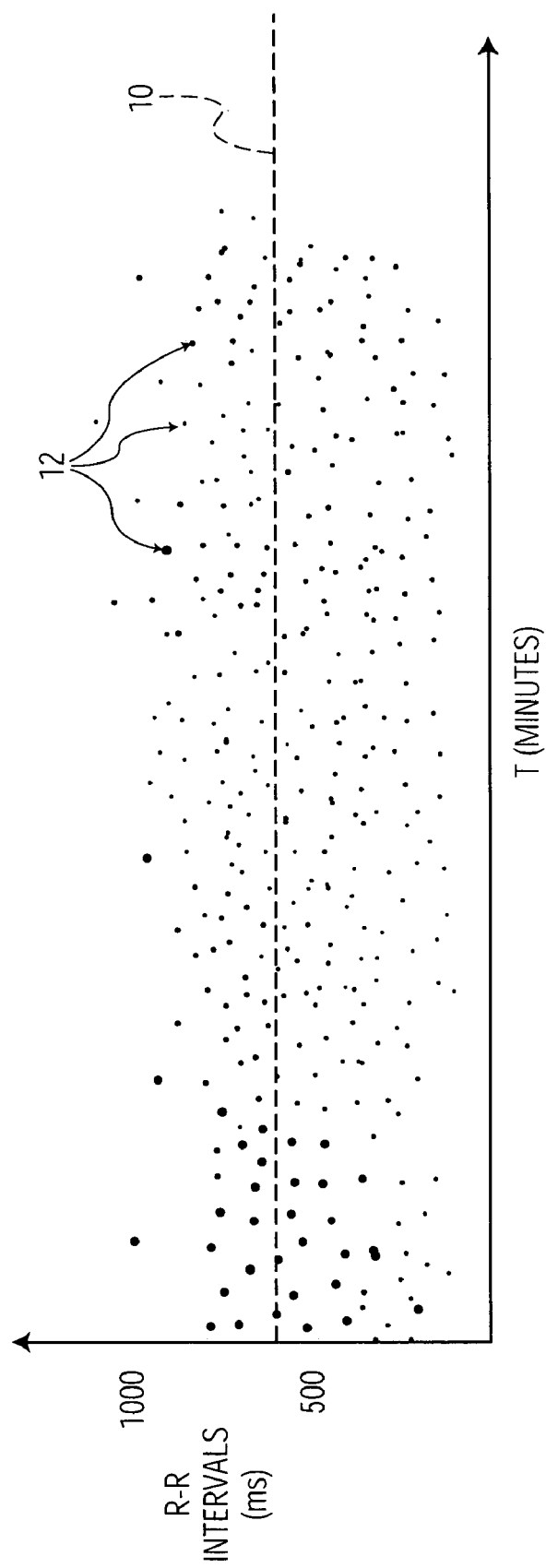
FIG. 2 is a plot of an R—R-interval distribution for a patient experiencing an AF episode.

In one embodiment, the analyze/synchronize circuit 42 determines whether the patient is experiencing an AF episode by analyzing the differences between the R—R intervals in the patient's electrocardiogram (FIG. 1). Specifically, the circuit 42 samples a plurality of consecutive R—R intervals, computes the respective differences between the length of each sampled R—R interval and the lengths of the adjacent R—R intervals, and determines that the patient is experiencing an AF episode if at least a predetermined number of these differences equals or exceeds a predetermined difference threshold. For example, suppose the number of samples is 20, the difference threshold is 40 ms, and the predetermined number is 5. Therefore, the circuit 42 detects an AF episode if 5 or more of the R—R-interval differences equal or exceed 40 ms. Alternatively, the circuit 42 may repeat this procedure for multiple groups of sampled R—R intervals and detect AF if the predetermined number of differences within each group equals or exceeds the predetermined difference threshold. For example, suppose there are 10 groups of 20 samples each. Therefore, the circuit 42 detects an AF episode if 5 or more of the R—R-interval differences within each group equal or exceed 40 ms. Circuits and techniques for performing such an R—R interval analysis are well known, and, therefore, are omitted for clarity.

In another embodiment, to increase diagnostic specificity, the analyze/synchronize circuit 42 determines whether the patient is experiencing an AF episode by analyzing the R—R intervals as discussed above and by analyzing the QRS signals of the patient's electrocardiogram. Referring to FIG. 1, a QRS signal is a combination of the Q, R, and S waves. During an AF episode, the patient's QRS signals typically have a normal shape. Therefore, the circuit 42 samples several of the QRS signals from the patient's electrocardiogram and compares each of their shapes to a normal QRS shape that is stored in the memory 44. (The normal QRS shape is the shape of a QRS signal that was previously sampled and stored while the patient was experiencing a normal heart rhythm.) If the respective differences between the shapes of the sampled QRS signals and the shape of the normal sinus rhythm QRS signal are all less than a predetermined QRS difference, then the circuit 42 determines that the sampled QRS signals are normal. Therefore, if the sampled QRS signals are normal and the R—R-interval analysis indicates an AF episode as discussed above, then the circuit 42 determines that the patient is experiencing an AF episode. If, however, the shapes of at least a predetermined number of the sampled QRS signals differ from the shape of the normal QRS signal by at least the predetermined QRS difference, then the circuit 42 determines that the sampled QRS signals are abnormal. Therefore, if the sampled QRS signals are abnormal, then the circuit 42 determines that the patient is not experiencing an AF episode regardless of the results of the R—R-interval analysis. Furthermore, because abnormal QRS signals may indicate a serious arrhythmia such as ventricular fibrillation (VF), the circuit 42 informs the operator and patient to seek prompt medical attention for the patient. Alternatively, the shock/analyze unit 24, upon identification of VF, may revert to a standard AED for VF. Circuits and techniques for comparing the shapes of QRS signals are well known, and, therefore, are omitted for clarity.

In yet another embodiment, the analyze/synchronize circuit 42 determines whether the patient is experiencing an AF episode by first determining the patient's heart rate and then performing either of the AF detection techniques discussed above. Typically, the heart rate of a patient experiencing an AF episode is in a range of approximately 40–200 beats per minute. Therefore, if the circuit 42 determines that the patient's heart rate is within this range, it proceeds with one of the AF-detection techniques as discussed above. Conversely, if the circuit 42 determines that the patient's heart rate is outside of this range, it informs the patient and operator that the patient is not experiencing an AF episode, and thus disables the shock-generator circuit 40 for atrial cardioversion. Circuits and techniques for determining a patient's heart rate are well known, and, therefore, are omitted for clarity.

Figure 5:
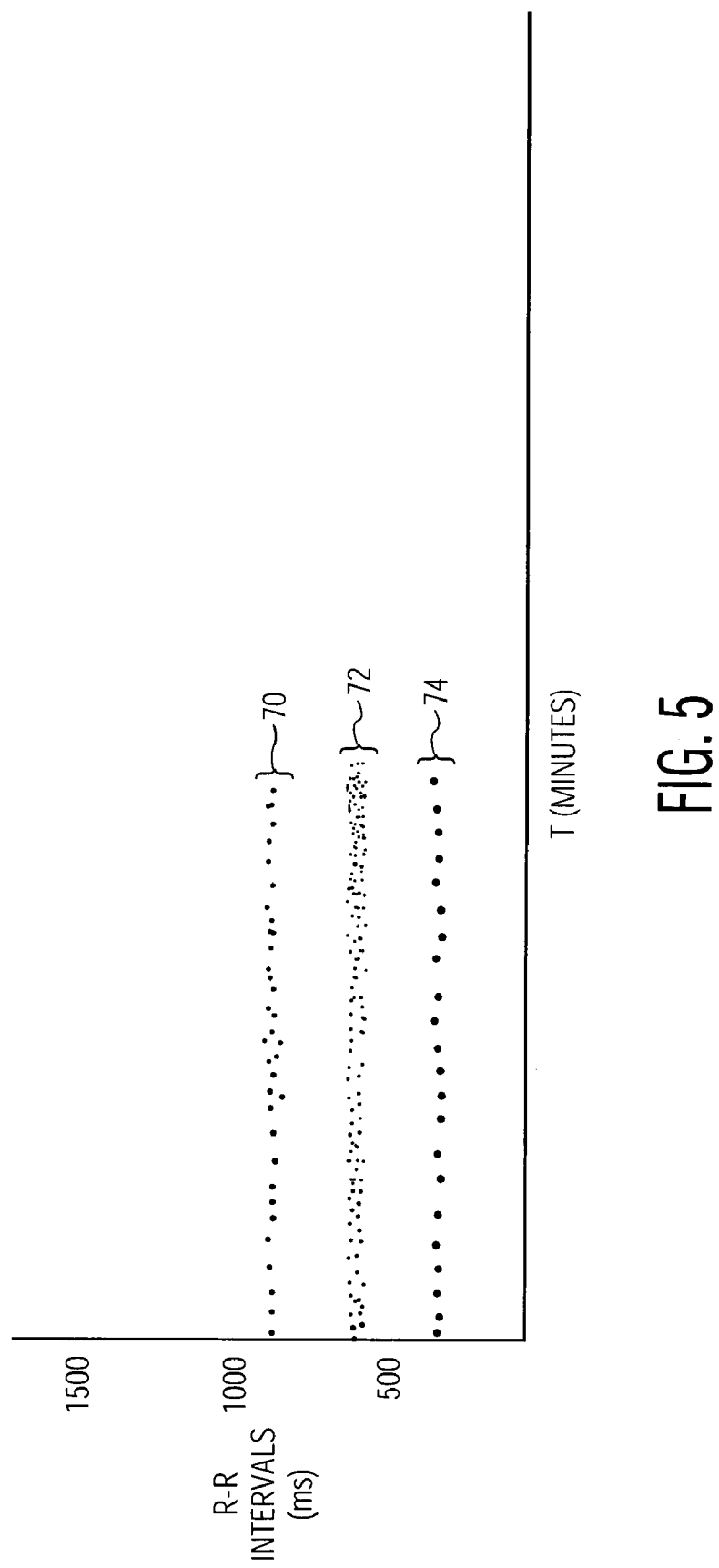
FIG. 5 is a plot of an R—R-interval distribution for a patient experiencing premature ventricular contractions (PVC).
Figure 6:
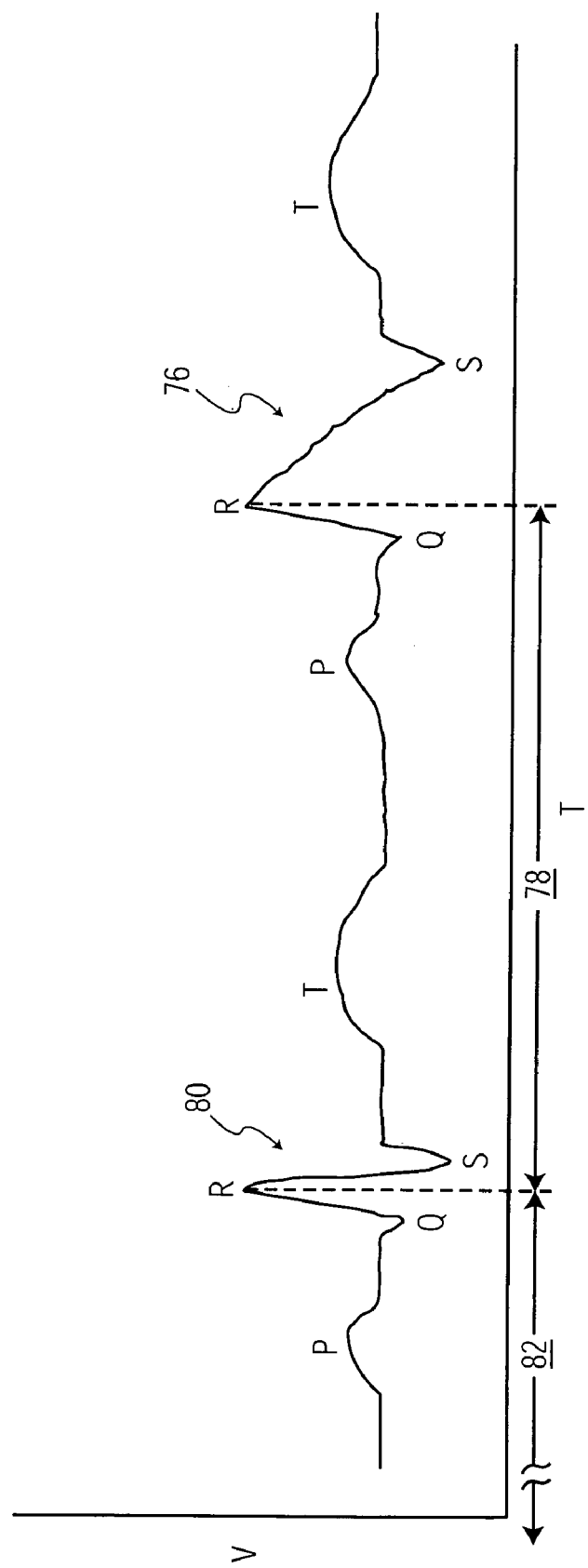
FIG. 6 is a portion of an electrocardiogram for a patient experiencing Ashman's phenomenon.

Referring to FIGS. 4, 5, and 6, in still another embodiment, the analyze/synchronize circuit 42 distinguishes between AF and other arrhythmias that the above-described AF-detection techniques may erroneously interpret as an AF episode. FIG. 5 is a plot of an R—R-interval distribution for a patient experiencing premature ventricular contractions (PVC). Like AF, the lengths of adjacent R—R intervals of a patient experiencing PVC can differ significantly. But unlike AF, the R—R-interval distribution for PVC lies primarily within three distribution regions 70, 72, and 74. Therefore, if the circuit 42 detects such a distribution pattern, it determines that the patient is not experiencing an AF episode even if the above-described R—R-interval analysis or combined R—R-interval/QRS analysis indicates otherwise. FIG. 6 is an electrocardiogram of a patient experiencing Ashman's phenomenon, which is characterized by a wider-than-normal QRS signal 76 that follows an Ashman sequence. An Ashman sequence includes a shorter-than-normal R—R interval 78, a normal QRS signal 80, and a longer-than-normal R—R interval 82 (only a portion of which is shown in FIG. 6). Because Ashman's phenomenon affects the QRS signals but not the R—R intervals, it is only a concern when the circuit 42 uses the combined R—R-interval/QRS analysis described above. Therefore, if the R—R-interval portion of the analysis indicates an AF episode but the QRS portion of the analysis indicates no AF episode, the circuit 42 determines whether the abnormal QRS signals follow respective Ashman sequences. If this is the case, then the circuit 42 determines that the patient is experiencing an AF episode regardless of the results of the QRS portion of the analysis. Circuits and techniques for detecting Ashman's sequences are well-known, and, therefore, are omitted for clarity.

Still referring to FIG. 4, in one embodiment, the analyze/synchronize circuit 42 synchronizes the generation of the ADF pulse to the rising edge of an R wave. Such synchronization reduces the chance that the ADF pulse will induce other more serious arrhythmia such as VF. Circuits and techniques for performing such synchronization are well-known, and, therefore, are omitted for clarity.

In another embodiment, the analyze/synchronize circuit 42 synchronizes the generation of the ADF pulse to the rising edge of an R wave that follows a normal or long R—R interval. This is because synchronizing an ADF pulse to an R wave that follows a short R—R interval increases the chances that the pulse will cause the patient to experience a more serious arrhythmia such as VF. A circuit and technique for performing such synchronization are discussed in U.S. Pat. No. 5,207,219 to Adams et al., which is incorporated by reference.

Still referring to FIG. 4, after the shock-generator circuit 40 generates the ADF pulse, the analyze/synchronize circuit 42 uses techniques similar to the AF-detection techniques discussed above to determine whether the AF episode has terminated. In one embodiment, the circuit 42 analyzes the differences between the R—R intervals in the patient's post-shock electrocardiogram and determines that the AF episode has terminated if at least a predetermined number of these differences is less than a predetermined difference threshold. For example, suppose that the number of samples is 20, and the difference threshold is 40 ms, and the predetermined number is 15. Therefore, the circuit 42 detects termination of the AF episode if at least 15 of the R—R-interval differences are less than 40 ms. In another embodiment, the circuit 42 also compares the post-shock QRS signals with the stored normal QRS signal. The circuit 42 detects that the AF episode has terminated if the post-shock QRS signals match the normal QRS signal and the results of the R—R-interval analysis indicate termination of the AF episode.

Although the shock/analyze unit 24 is described in conjunction with FIG. 4 as including a number of functional circuit blocks, the unit 24 may instead include one or more processors that are programmed to perform the functions of these circuit blocks.

Figure 7:
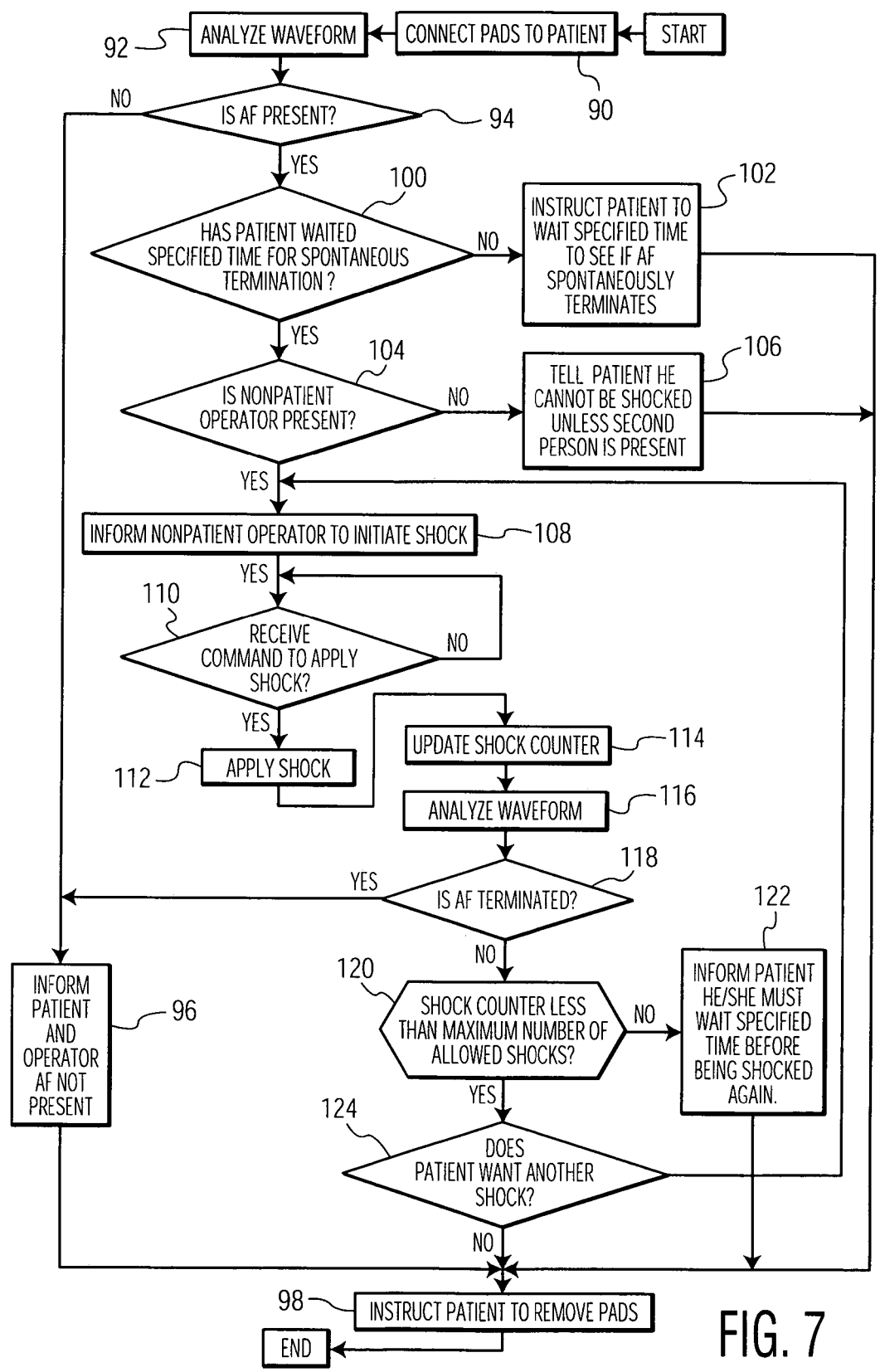
FIG. 7 is a flow diagram of an atrial-defibrillation procedure that incorporates the atrial defibrillator of FIG. 3 according to an embodiment of the invention.

FIG. 7 is a flow diagram of an atrial defibrillation procedure that incorporates the atrial defibrillator 20 of FIG. 3 according to an embodiment of the invention.

Referring to block 90, the operator activates the defibrillator 20 and attaches the pads 26 and 28 to the patient's body (FIG. 3).

Referring to blocks 92 and 94, the defibrillator 20 analyzes the patient's cardiac signal and determines whether the patient is experiencing an AF episode as discussed above in conjunction with FIGS. 4, 5, and 6. Referring to blocks 96 and 98, if the patient is not experiencing an AF episode, then the defibrillator 20 informs the patient and operator and instructs the operator to remove the pads 26 and 28 from the patient.

Referring to blocks 100 and 102, if the patient is experiencing an AF episode, then the defibrillator 20 "asks" the patient if he/she has waited for at least a specified waiting period since the onset of the AF episode. Such a waiting period allows the AF episode a chance to spontaneously terminate without the need for an ADF shock. In one embodiment, the waiting period is approximately 6 hours. The patient or the operator enters a "yes" or "no" response. If a "no" is entered, then the defibrillator 20 instructs the operator to remove the pads 26 and 28 (block 98) and to wait the remainder of the waiting period before using the defibrillator 20.

Referring to block 104, if the patient has waited for at least the specified waiting period, then the defibrillator asks him/her if there is another authorized person, i.e., the operator, available to administer the ADF shock. If the patient answers "no", then, referring to blocks 106 and 98, the defibrillator 20 informs the patient that he cannot shock himself and instructs the patient to remove the pads 26 and 28. As discussed above, the patient is not allowed to shock himself for safety reasons. For example, there is a very small risk that an ADF pulse, even if properly synchronized to the cardiac signal, may cause the patient to experience VF. A patient is typically unconscious during a VF episode, which can lead to the patient's death. Therefore, if the ADF shock induces VF and no other person is present, then the patient, who will be unable to call for help, will die. The presence of an operator, however, allows the rare induction of VF to be promptly treated with the defibrillator 20 or a portable VF defibrillator (not shown) and allows the operator to call an ambulance and even administer cardiopulmonary resuscitation (CPR). For additional safety, the identification verifier 32 (FIGS. 3 and 4) insures that only an authorized operator can initiate the ADF shock. For example, the verifier 32 may require the operator to enter a secret code or may scan a physical characteristic such as a fingerprint or retina and compare it to an image of the characteristic stored in the memory 44. Or, the defibrillator 20 may include circuitry that determines whether the operator is attached to the pads 26 and 28. If the operator is so attached, then the defibrillator 20 determines that the operator is actually the patient and is attempting to shock himself, and thus disables the shock-generator circuit 40.

Referring to block 108, if an authorized operator is present, then the defibrillator 20 informs him that he/she can initiate an ADF shock when the patient is ready. For example, the patient may want to delay the initiation of the shock for several hours so that he/she can take a sedative such as Valium and allow the sedative sufficient time to take effect. Once the patient is ready and the diagnostic algorithm is satisfied, the operator initiates the ADF shock by entering a shock command via the control panel 32 (FIGS. 3 and 4).

Referring to block 110, the defibrillator 20 waits for the operator to enter the shock command. Referring to blocks 112 and 114, once the operator enters the shock command, the defibrillator 20 generates and delivers the shock to the patient and updates the shock counter 58 (FIG. 4), which the defibrillator previously reset to an initial count value such as zero.

Referring to blocks 116 and 118, the defibrillator 20 analyzes the post-shock cardiac signal from the patient and determines whether the AF episode has terminated. In one embodiment, the defibrillator 20 uses one or more of the AF-termination-detection procedures discussed above in conjunction with FIGS. 4, 5, and 6.

Referring to blocks 96 and 98, if the AF episode has terminated, then the defibrillator 20 informs the patient and operator and instructs the operator to remove the pads 26 and 28 from the patient.

Referring to block 120, if the AF episode has not terminated, then the defibrillator 20 checks the shock counter 58 (FIG. 4) to determine if more shocks are available for the present session.

Referring to block 122, if there are no more shocks available in the present session, then the defibrillator 20 instructs the patient to call his cardiologist and wait a specified time before the next session. Next, referring to block 98, the defibrillator 20 instructs the operator to remove the pads 26 and 28 from the patient.

Referring to block 124, if there are more shocks available in the present session, then the defibrillator 20 asks the patient if he would like another shock. Referring to block 108, if the patient answers "yes", then the defibrillator instructs the operator to initiate the shock. Referring to block 98, if the patient answers "no", then the defibrillator instructs the operator to remove the pads 26 and 28 from the patient.

From the foregoing it will be appreciated that, although specific embodiments of the invention have been described herein for purposes of illustration, various modifications may be made without deviating from the spirit and scope of the invention.

What is claimed is:

1. A method, comprising:
 receiving a cardiac signal from a patient;
 determining from the signal whether the patient is experiencing atrial fibrillation;
 receiving a shock command from an operator; and
 shocking the patient with a portable shock generator in response to the shock command if the patient is experiencing atrial fibrillation,
 wherein the determining comprises:
 measuring the lengths of R—R intervals in the signal;
 calculating the respective differences between the lengths of contiguous ones of the R—R intervals;
 comparing the calculated differences to a difference threshold; and
 determining that the patient is not in atrial fibrillation if one of the calculated differences is less than the difference threshold.

2. A nonsurgical method of treating atrial fibrillation, comprising:
 transdermally receiving a cardiac signal from a patient;
 determining from the signal whether the patient is experiencing atrial fibrillation;
 verifying the presence of an authorized operator;
 applying a shock enable signal to a portable shock generator if the patient is experiencing atrial fibrillation;
 shocking the patient with the portable shock generator external to the patient if the patient is experiencing atrial fibrillation and an authorized operator is present; and
 wherein the determining comprises,
 determining the patient's heart rate and
 determining that the patient is not in atrial fibrillation if the heart rate is outside of a predetermined range.

3. A method, comprising:
 receiving a cardiac signal from a patient;
 determining from the signal whether the patient is experiencing atrial fibrillation;
 shocking the patient with a portable shock generator if the patient is experiencing atrial fibrillation;
 storing a normal QRS signal of the patient; and
 wherein the determining comprises;
 measuring the lengths of R—R intervals of the cardiac signal,
 calculating the respective differences between the lengths of contiguous ones of the R—R intervals,
 comparing the calculated differences to an R—R threshold,
 calculating a difference between a QRS signal of the cardiac signal and the stored QRS signal,
 comparing the calculated QRS difference to a QRS threshold, and
 determining that the patient is not in atrial fibrillation if one of the calculated differences is less than the R—R threshold or if the QRS difference is greater than or equal to the QRS threshold.

4. A method, comprising:
 receiving a cardiac signal from a patient;
 determining from the signal whether the patient is experiencing atrial fibrillation;
 identifying an operator of a shock generator;
 enabling the shock generator if the operator is authorized to operate the shock generator; and
 shocking the patient with the shock generator in response to a shock command from the operator if the patient is experiencing atrial fibrillation.

5. The method of claim 4, further comprising disabling the shock generator if the operator is identified as the patient.

6. The method of claim 4 wherein the patient is the operator.

7. A nonsurgical method of treating atrial fibrillation, comprising:
 transdermally receiving a cardiac signal from a patient by a transdermal electrode;
 determining from the signal with a portable external analyzer whether the patient is experiencing atrial fibrillation;
 determining the presence of an authorized operator;
 enabling a portable shock generator with a signal from the portable analyzer;
 receiving a shock command from an authorized operator; and
 shocking the patient with the portable shock generator by means of the transdermal electrode in response to the shock command if the patient is experiencing atrial fibrillation.

8. The method of claim 7, further comprising determining from the cardiac signal with the portable analyzer whether the atrial fibrillation terminates after shocking the patient.

9. The method of claim 7 wherein the shocking comprises shocking the patient during a rising edge of an R wave in the cardiac signal.

10. A nonsurgical method of treating atrial fibrillation, comprising:
receiving a cardiac signal from a patient;
determining from the signal with a portable external analyzer whether the patient is experiencing atrial fibrillation;
informing the patient by means of the analyzer that the patient is experiencing atrial fibrillation;
receiving a shock command from an operator; and
shocking the patient with a portable shock generator in response to the shock command if the patient is experiencing atrial fibrillation, further comprising:
applying defibrillator pads to the patient;
wherein the receiving comprises receiving the cardiac signal via the pads, and
wherein the shocking comprises shocking the patient via the pads.

11. An atrial defibrillator, comprising:
a portable, non-implantable housing;
a pair of defibrillator pads operable to be applied to the outside of a patient's body;
a shock generator disposed in the housing, coupled to the pads, and operable to shock the patient via the pads;
an analyzer disposed in the housing and operable to receive a cardiac signal from the patient, to determine from the signal whether the patient is experiencing atrial fibrillation, and to enable the shock generator if the patient is experiencing atrial fibrillation;
wherein the cardiac signal comprises an electrocardiogram having R—R intervals; and
the analyzer is operable to determine whether the patient is experiencing atrial fibrillation by;
measuring the durations of the R—R intervals,
calculating the respective differences between the lengths of contiguous ones of the R—R intervals,
comparing the calculated differences to a difference threshold, and
determining that the patient is experiencing atrial fibrillation if one of the calculated differences exceeds the threshold.

12. An atrial defibrillator, comprising:
a portable, non-implantable housing;
a pair of defibrillator pads operable to be applied to the outside of a patient's body;
a shock generator disposed in the housing, coupled to the pads, and operable to shock the patient via the pads;
an analyzer disposed in the housing and operable to receive a cardiac signal from the patient, to determine from the signal whether the patient is experiencing atrial fibrillation, and to enable the shock generator if the patient is experiencing atrial fibrillation;
wherein the cardiac signal comprises an electrocardiogram having R—R intervals; and
wherein the analyzer is further operable to determine from the cardiac signal whether the atrial fibrillation terminates after the shock generator shocks the patient by;
measuring the lengths of the R—R intervals,
calculating respective differences between the lengths of continuous ones of the R—R intervals,
comparing the calculated differences to a difference threshold, and
determining that the atrial fibrillation is terminated if one of the calculated differences is less than the difference threshold.

13. An atrial defibrillator, comprising:
a portable, non-implantable housing;
a pair of defibrillator pads operable to be applied to the outside of a patient's body;
a shock generator disposed in the housing, coupled to the pads, and operable to shock the patient via the pads; and
an analyzer disposed in the housing and operable to receive a cardiac signal from the patient, to determine from the signal whether the patient is experiencing atrial fibrillation, and to enable the shock generator if the patient is experiencing atrial fibrillation;
wherein the cardiac signal comprises an electrocardiogram having R—R intervals; and
wherein the analyzer is operable to determine whether the patient is experiencing atrial fibrillation by;
measuring the durations of the R—R intervals, calculating respective differences between the lengths of contiguous ones of the R—R intervals,
comparing the calculated differences to a difference threshold,
determining the patient's heart rate,
determining whether the patient's heart rate is within a predetermined range of heart rates, and
determining that the patient is experiencing atrial fibrillation if one of the differences exceeds the threshold and the heart rate is within the predetermined range.

14. An atrial defibrillator, comprising:
a portable, non-implantable housing;
a pair of defibrillator pads operable to be applied to the outside of a patient's body;
a shock generator disposed in the housing, coupled to the pads, and operable to shock the patient via the pads;
an analyzer disposed in the housing and operable to receive a cardiac signal from the patient, to determine from the signal whether the patient is experiencing atrial fibrillation, and to enable the shock generator if the patient is experiencing atrial fibrillation;
wherein the cardiac signal comprises an electrocardiogram having R—R intervals; and
wherein the analyzer is operable to determine whether the patient is experiencing atrial fibrillation by;
measuring the durations of a first group of the R—R intervals,
calculating the respective differences between the durations of contiguous ones of the R—R intervals in the first group,
comparing the calculated differences to a difference threshold,
repeating the measuring, calculating, and comparing for a second group of the R—R intervals, and
determining that the patient is experiencing atrial fibrillation if one of the first-group differences and one of the second-group differences exceed the threshold.

15. An atrial defibrillator, comprising:
a portable, non-implantable housing;
a pair of defibrillator pads operable to be applied to the outside of a patient's body;
a shock generator disposed in the housing, coupled to the pads, and operable to shock the patient via the pads;
an analyzer disposed in the housing and operable to receive a cardiac signal from the patient, to determine from the signal whether the patient is experiencing atrial fibrillation, and to enable the shock generator if the patient is experiencing atrial fibrillation;
a memory coupled to the analyzer and operable to store a normal QRS signal of the patient;
wherein the cardiac signal comprises an electrocardiogram having QRS signals and R—R intervals; and
wherein the analyzer is operable to determine whether the patient is experiencing atrial fibrillation by;
measuring the durations of the R—R intervals,
calculating respective R—R differences between the lengths of contiguous ones of the R—R intervals,
comparing the calculated R—R differences to an R—R threshold,
calculating a QRS difference between one of the QRS signals of the cardiac signal and the stored QRS signal,
comparing the calculated QRS difference to a QRS threshold, and
determining that the patient is experiencing atrial fibrillation if one of the R—R differences equals or exceeds the R—R threshold and the QRS difference is less than the QRS threshold.

16. An atrial defibrillator, comprising:
a portable, non-implanting housing;
a pair of defibrillator pads operable to be applied to the outside of a patient's body;
a shock generator disposed in housing, coupled to the pads, and operable to shock the patient via the pads;
an analyzer disposed in the housing and operable to receive a cardiac signal from the patient, to determine from the signal whether the patient is experiencing atrial fibrillation, and to enable the shock generator if the patient is experiencing atrial fibrillation; and
a safety device disposed in the housing and operable to prevent the patient from activating the shock generator.

17. An atrial defibrillator comprising:
a portable, non-implanting housing;
a pair of defibrillator pads operable to be applied to the outside of a patient's body;
a shock generator disposed in the housing, coupled to the pads, and operable to shock the patient via the pads;
an analyzer disposed in the housing and operable to receive a cardiac signal from the patient, to determine from the signal whether the patient is experiencing atrial fibrillation, and to enable the shock generator if the patient is experiencing atrial fibrillation; and
a verification device disposed in the housing and operable to prevent an unauthorized person from activating the shock generator.

18. An atrial defibrillator, comprising:
a portable, non-implantable housing;
a pair of defibrillator pads operable to be applied to the outside of a patient's body;
a shock control operable to allow a patient to defer a self-administered shock;
a shock generator disposed in the housing and responsive to the shock control, coupled to the pads, and operable to shock the patient via the pads with a multi-phasic waveform; and
an analyzer disposed in the housing and operable to receive a cardiac signal from the patient, to determine from the signal whether the patient is experiencing atrial fibrillation, and to enable the shock generator if the patient is experiencing atrial fibrillation.

* * * * *